(12) United States Patent
Ferguson-Smith et al.

(10) Patent No.: US 6,255,465 B1
(45) Date of Patent: *Jul. 3, 2001

(54) CROSS-SPECIES CHROMOSOME PAINTING

(75) Inventors: Malcolm A Ferguson-Smith, Cambridge (GB); Johannes F Wienberg, Reischenhart; Stefan Muller, Munich, both of (DE)

(73) Assignee: Cambridge University Technical Services Ltd., Cambridge (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/032,346

(22) Filed: Feb. 27, 1998

(30) Foreign Application Priority Data

Feb. 27, 1997 (GB) .................................................. 9704054

(51) Int. Cl.[7] .......................... C07H 21/02; C07H 21/04; C12Q 1/68

(52) U.S. Cl. .................... 536/23.1; 536/24.3; 536/24.31; 435/6

(58) Field of Search ............................... 536/24.3, 24.31, 536/23.1; 435/6

(56) References Cited

U.S. PATENT DOCUMENTS

| | | | |
|---|---|---|---|
| 5,447,841 | 9/1995 | Gray et al. | 435/6 |
| 5,665,549 | 9/1997 | Pinkel et al. | 435/6 |
| 5,798,262 | 8/1998 | Garini et al. | 435/287.2 |
| 5,817,462 | 10/1998 | Garini et al. | 435/6 |
| 5,843,649 | * 12/1998 | Stoerker | 435/6 |

FOREIGN PATENT DOCUMENTS

WO 97/22848  6/1997 (WO).

OTHER PUBLICATIONS

Scherthan et al (1994). Nature Genetics 6:342–347, Apr. 1994.*
Arnold et al (1996). Cytogenetics and Cell Genetics 74:80–85, 1996.*
Ahern (1995). The Scientist 9:20, Jul. 1995.*
Kim et al (1996). Chromosome Research 4:500–506, 1996.*
Arnold et al, "Identification of Complex Chromsome Rearrangement in the Gibbon by Fluorescent In Situ Hybridization (fish) of a Human Chromosomes, and Reciprocal Chromsome Painting", Cytogenet Cell Genet, 74:80–85 (1996).*
Jauch et al., "Reconstruction of Genomic Rearrangements in Great Apes and Gibbons by Chromosome Painting". Proc. Natl. Acad. Sci. USA, 89:8611–8615 (1992).
Koehler et al., "Genomic Reorganization and Disrupted Chromosomal Synteny in the Siamang (*Hylobates Syndactylus*) Revealed by Fluorescence in Situ Hybridization", American Journal of Physical Anthropology, 97:37–47 (1995).
Koehler et al., "Genomic Reorganization in the Concolor Gibbon (*Hylobates Concolor*) Revealed by Chromosome Painting", Genomics 30:287–292 (1995).
Stanyon et al., "Chromosomal Painting Shows that "Marked Chromosomes" In Lesser Apes and Old World Monkeys are not Homologous and Evolved by Convergence", Cytogenet Cell Genet 68:74–78 (1995).

(List continued on next page.)

*Primary Examiner*—Carla J. Myers
*Assistant Examiner*—Diana Johannsen
(74) *Attorney, Agent, or Firm*—Townsend & Townsend & Crew LLP (57) ABSTRACT

The invention provides methods and reagents for detecting a chromosomal aberration in an animal chromosome or karyotype. One or more detectably-labeled chromosome-specific probes from a first animal species are hybridized to chromosomes of a second animal species. This results in a banding pattern that can be compared to the pattern found in a normal chromosome or karyotype.

7 Claims, 5 Drawing Sheets

OTHER PUBLICATIONS

Ferguson–Smith, M.A., "Genetic Analysis by Chromosome Sorting and Painting: Phylogenetic and Diagnostic Applications" *Eur. J. Hum. Genet.* 5:253–265 (1997).

Goureau, A. et al., "Human and porcine correspondence of chromosome segments using bidirectional chromosome painting" *Genomics* 36 (2) :252–262 (Sep. 1, 1996).

Koehler, U. et al., "Genomic Reorganization in the Concolor Gibbon (*Hylobates concolor*) Revealed by Chromosome Painting" *Genomics* 30 :287–292 (1995).

Müller, S. et al., "A novel source of highly specific chromosome painting probes for human karyotype analysis derived from primate homologues" *Hum. Genet.* 101:149–153 (1997).

Müller, S. et al., "Toward a multicolor chromosome bar code for the entire human karyotype by fluorescence in situ hybridization" *Hum. Genet.* 100:271–278 (1997).

Pinkel, D. et al., "Flourescence in situ hybridization with human chromosome–specific libraries: Detection of trisomy 21 and translocations of chromosome 4" *Proc. Natl. Acad. Sci. USA* 89 :1388–1392 (1992).

Rabbitts, P. et al., "Chromosome specific paints from a high resolution flow karyotype of the mouse" *Nature Genet.* 9:369–375 (Apr. 1995).

Richard, F. et al., "ZOO–FISH suggests a complete homology between human and capuchin monkey (Platyrrhini) euchromatin" *Genomics* 36(3) :417–423 (Sep. 15, 1996).

Ried, T. et al., "Simultaneous visualization of seven different DNA probes by in situ hybridization using combinatorial fluorescence and digital imaging microscopy" *Proc. Natl. Acad. Sci. USA* 89:1388–1392 (Feb. 1992).

Telenius, H. et al., "Cytogenetic analysis by chromosome painting using DOP–PCR amplified flow–sorted chromosomes" *Genes, Chromosomes & Cancer* 4:257–263 (1992).

Wienberg, J. et al., "Conservation of human vs. feline genome organization revealed by reciprocal chromosome painting" *Cytogenet. Cell Genet.* 77(3–4) :211–217 (1997).

Wienberg, J. et al., "Chromosome painting without competitor DNA" *Elsevier Trends Journals Technical Tips Online*, 2 pages (Jan. 22, 1997) www.elsevier.com/locate/tto.

Wienberg, J. et al., "Chromosome painting in mammals as an approach to comparative genomics" *Curr. Opinion Genet. Devel.* 5:792–797 (1995).

Yang, F. et al., "Comparative chromosome painting in mammals: human and the Indian muntjac (*Muntiacus muntjak vaginalis*)" *Genomics* 39(3) :396–401 (Feb. 1, 1997).

Cambio Ltd. Catalog, pp. 1, 19, 20 "Star*Fish™ Chromosome Painting" Undated.

Ferguson–Smith, "Applications of Cross–Species Color Banding" (Abstract), 47th ASHG Annual Meeting, Baltimore, Maryland, Oct. 29, 1997.

Muller, "Cross–Species Color Banding (CSC–Banding) : Technical Aspects" (Abstract), 47th ASHG Annual Meeting, Baltimore, Maryland, Oct. 29, 1997.

Wienberg, "Cross–Speciecs Chromosome Painting in Human Karyotype Analysis" (Abstract), 47th ASHG Annual Meeting, Baltimore, Maryland, Oct. 29, 1997.

* cited by examiner

CROSS-SPECIES CHROMOSOME PAINTING

PRIORITY

This application claims priority to British Patent Application No. 9704054.7, filed on Feb. 27, 1997, the content of which is explicitly incorporated by reference in its entirety.

FIELD OF THE INVENTION

This invention relates to an assay for the detection and identification of chromosomal aberrations.

BACKGROUND TO THE INVENTION

The identification and analysis of chromosome preparations has previously depended on staining methods which produce characteristic chromosome banding patterns unique for every chromosome. The resolution of the method is low, and small rearrangements, including some deletions and duplications, are undetectable. This has led to the introduction of fluorescence in situ hybridization (FISH) techniques using DNA probes which can anneal to complementary sequences on chromosomes and thus act as specific markers. The probes annealed in this way are commonly labeled by haptens and detected indirectly by fluorescent-antibodies, or detected directly by fluorochromes incorporated into the probe itself. The specificity of the probe depends on its DNA sequence and the size of the signal depends on the length of the sequence. Many types of DNA probe are cloned in plasmid, cosmid, yeast artificial chromosome or other vector.

Another class of DNA probe uses total genomic DNA from either complete nuclear DNA or from fractions of nuclear DNA, which can be generated from a variety of sources including whole cells and specific chromosomes. The usual method of preparing these complex probes is by DNA amplification using the polymerase chain reaction (PCR) and random DNA primers. The label is incorporated during the amplification procedure or by nick-translation following amplification. Hybridization of these probes to chromosomes results in a more or less uniform series of fluorescent signals throughout the length of the chromosome. This has been referred to as "chromosome painting" and the probes producing this effect have been termed chromosome paints.

Paints corresponding to individual chromosomes (chromosome-specific paints) can be prepared from PCR amplification of flow sorted chromosomes. They have proved to be useful in the detection and identification of chromosome aberrations beyond the resolution of standard cytogenetic banding methods. Several chromosome specific paints can be used together to detect multiple target chromosomes provided different fluorochromes are used for labeling the probes derived from different chromosomes. For a more detailed description of modem cytogenetic techniques see Ferguson-Smith and Andrews, 1996, "Cytogenetic Analysis," Chapter 12 in Emery & Rimoin's PRINCIPLES & PRACTICE OF MEDICAL GENETICS, edited by D. L. Rimoin et al., Churchill-Livingstone, London. In addition, human chromosome specific paints have been used to identify homologies in non-human species by comparative genome analysis (Wienberg & Stanyon, 1995, *Curr. Opin. Gen. & Dev.* 5:792–97).

SUMMARY OF THE INVENTION

In one aspect, the present invention provides a method for detecting a chromosomal aberration in an animal, by hybridizing at least one detectably-labeled chromosome-specific probe from a first animal species to one or more chromosomes of a second animal species; detecting a banding pattern resulting from the hybridization; and comparing the banding pattern detected to a banding pattern for the corresponding non-aberrant chromosome(s) of the second species. In one embodiment of this method, a plurality (at least two) of detectably-labeled chromosome-specific probes from the first animal species are hybridized to one or more chromosomes of a second animal species, and at least a two of the chromosome-specific probes are differently labeled.

In one embodiment of the invention, both animal species are vertebrate. In various embodiments, the first animal species is a non-human primate, for example a non-human primate of the genus Hylobates, such as *Hylobates concolor* and/or *Hylobates syndactylus*. In one embodiment of the invention, the second species is a human. The hybridization may be to the complete karyotype of the second animal.

The probes of the invention may be detectably labeled probes with one or more hapten species, a fluorochrome, or both. In certain embodiments, the hapten is biotin, digoxigenin, or fluorescein-isothiocyanate (FITC). Examples of fluorochromes are FITC, Cyanine-2, Cyanine-3, Cyanine-3.5, Cyanine-5, Cyanine-7, fluorescein, Texas red, rhodamine, lissamine and phycoerythrin. Chromosome-specific probes of the invention may be labeled with more than one label (e.g., 2, 3 or more haptens, fluorochromes, or combinations of haptens and flurochromes).

In a related aspect, the invention is directed to compositions of detectably-labeled chromosome-specific probes from at least two different animal species. The species may be vertebrates such as non-hunan primates (e.g., species from the genus Hylobates, such as *Hylobates concolor* and *Hylobates syndactylus*).

In another related aspect, the invention provides kits useful for detecting chromosome aberrations. In one embodiment, the kit contains one or more detectably labeled chromosome-specific probes from a non-human animal species, and a photograph or drawing of a normal human karyotype stained with the probes. In one embodiment, the kit of the invention contains detectably labeled chromosome-specific probes from two different species in the same container. In a particular embodiment, both species are non-human primates such as primates of genus Hylobates.

BRIEF DESCRIPTION OF THE FIGURES

Probes were from the *H. concolor* (Concolor) gibbon chromosomes: (a) chromosome 5; (b) chromosome 9; (c) chromosome 12; and (d) chromosome 24. The normal human chromosome is on the left side of each image. A band not labeled with gibbon chromosome 12 probe in (c) in the short arm corresponds to the segment painted with part of the chromosome 5 probe. This segment is transposed and inserted close to the telomere (a) disrupting the signal of the gibbon chromosome 24 probe (d).

DESCRIPTION OF THE INVENTION

Prior to the present invention, the usefulness of chromosome painting for karyotype analysis has been limited. Although conventional chromosome painting can be used to detect interchromosomal rearrangements, such as translocations, it cannot identify intrachromosomal rearrangements such as inversions, amplifications and deletions. Thus, a method that facilitates the detection of intrachromosomal rearrangements would greatly improve the analysis of chromosome aberrations. Another limitation of previous methods of chromosome painting is the cross-hybridization which occurs between certain non-homologous chromosomes due to the presence of various classes of repetitive DNA. Some, but not all, of the cross-hybridization can be eliminated by blocking with Cot-1 DNA or allowing the probe to pre-anneal with itself before hybridizing to the chromosome preparation (Wienberg et al., 1997, "Chromosome painting without competitor DNA" *Technical Tips Online* (http//www.elsevier.com/locate/tto). However, using these methods background (cross-hybridization) is still observed for probes derived from certain chromosomes.

The present invention provides methods and reagents for detecting a chromosomal aberration in an animal, using chromosome specific paints (e.g., prepared by the differential labeling of chromosome arms, regions and subregions) prepared from species which have diverged from one another in repetitive DNA. In addition, subregional characterization is achieved where chromosomal rearrangements have occurred during divergence. In one embodiment, an in situ hybridization FISH system is used to label each chromosome specific probe with a distinctive spectrum of fluorochromes. This is achieved by combining fluorochromes in different combinations and ratios for each chromosome. The chromosome specific probes are pooled in a hybridization probe mixture (the CSC-banding probe), and hybridized to the chromosome preparation from the diverged species. Depending on the number of chromosome rearrangements which have occurred during the divergence of the two species, each target chromosome will appear under the fluorescence microscope to be composed of a series of differently colored blocks of conserved DNA. These differently colored blocks are referred to herein as "bands", and the process of producing them is referred to as "cross-species color banding," or CSC-banding. By comparing the banding pattern of the subject chromosome or karyotype to that of a normal, or non-aberrant, chromosome or karyotype, chromosome abnormalities are identified.

The method and novel reagents of the invention are useful for, among other uses, the analysis of human chromosome aberrations in clinical diagnosis and in cancer cytogenetics. Additional applications include studies in animal cytogenetics and as biological dosimeter for clastogenic agents in mutation studies using cell cultures or animal models. The present method has numerous advantages over conventional banding (e.g., by 4,6-diarninido-2-phenylindole [DAPI] staining) or conventional FISH methods, including:

1) Intrachromosomal rearrangements can be identified in addition to interchromosomal aberrations and aneuploidies.
2) Cross-hybridization between non-homologous chromosomes is greatly reduced, in part due to extensive divergence of repetitive DNA sequences between species. Unique sequence DNA is, on the other hand, conserved between species.

The reduction in cross hybridization allows improved specificity, a pre-requisite for automated chromosome analysis.

3) As stable sources of chromosome specific DNA paint probes are used, the method is highly reproducible.
4) The method can be used in conjunction with many techniques, including standard fluorescence microscopy, combinatorial multi-fluor FISH, and with spectral karyotyping.

The invention will now be described in additional detail.

I. Definitions

The term "chromosome banding" refers to differential staining of chromosomes resulting in a pattern of transverse bands of distinguishable (e.g., differently or alternately colored) regions, that is characteristic for the individual chromosome or chromosome region (i.e., the "banding pattern"). Conventional banding techniques include G-banding (Giemsa stain), Q-banding (Quinacrine mustard stain), R-banding (reverse-Giemsa), and C-banding (centromere banding).

The term "karyotype" refers to the chromosome characteristics of an individual cell or cell line of a given species, as defined by both the number and morphology of the chromosomes. Typically, the karyotype is presented as a systematized array of prophase or metaphase (or otherwise condensed) chromosomes from a photomicrograph or computer-generated image. Alternatively, interphase chromosomes may be examined as histone-depleted DNA fibers released from interphase cell nuclei.

As used herein, "chromosomal aberration" or "chromosome abnormality" refers to a deviation between the structure of the subject chromosome or karyotype and a normal (i.e., "non-aberrant") homologous chromosome or karyotype. The terms "normal" or "non-aberrant," when referring to chromosomes or karyotypes, refer to the predominate karyotype or banding pattern found in healthy individuals of a particular species and gender. Chromosome abnormalities can be numerical or structural in nature, and include aneuploidy, polyploidy, inversion, translocation, deletion, duplication, and the like. Chromosome abnormalities may be correlated with the presence of a pathological condition (e.g., trisomy 21 in Down syndrome, chromosome 5p deletion in the cri-du-chat syndrome, and a wide variety of unbalanced chromosomal rearrangements leading to dysmorphology and mental impairment) or with a predisposition to developing a pathological condition.

"Chromosome-specific probe" or "chromosome-specific paint" refers to a combination of detectably labeled polynucleotides that have sequences corresponding to (e.g., essentially the same as) the sequences of DNA from a particular chromosome or subchromosomal region of a particular chromosome (e.g., a chromosome arm). Typically, the chromosome-specific probe is produced by amplification (e.g., using the polymerase chain reaction) of the corresponding chromosomal DNA. A chromosome-specific probe will hybridize in an essentially uniform pattern along the chromosome or subchromosomal region from which it is derived.

The term "CSC-banding probe" or "CSC-banding paint" refers to a mixture of chromosome-specific probes. The CSC-banding probes of the invention typically comprise a mixture of at least two, usually many, chromosome-specific probes.

The term "detectable label" refers in a general sense to a moiety, such as a radioactive isotope or group containing same, and nonisotopic labels, such as enzymes, biotin, avidin, streptavidin, digoxygenin, luminescent agents, dyes, haptens, and the like. Luminescent agents, depending upon the source of exciting energy, can be classified as radioluminescent, chemiluminescent, bioluminescent, and photoluminescent (including fluorescent and phosphorescent). The term "fluorescent" refers to the property of a substance (such as a fluorophore) to produce light while it is being acted upon by radiant energy, such as ultraviolet light or X-rays. A probe or paint is "detectably labeled" when it is chemically combined or associated with a detectable label.

The term "directly labeled" denotes a polynucleotide probe with a detectable label that is detectable after hybridization with a target nucleic acid without further reactive processing. An example is a polynucleotide labeled with fluorescein-isothiocyanate conjugated dUTP.

The term "indirectly labeled" denotes a polynucleotide probe with a detectable label that, after hybrid formation with a target, must be further reacted in subsequent processing with one or more reagents to associate therewith one or more moieties that finally result in a detectable entity. An example is a polynucleotide labeled with digoxigenin-conjugated dUTP which can be visualized using a fluorochrome-conjugated anti-digoxigenin antibody.

Nucleic probes are "derived" from a particular chromosome or chromosome region when the probes have nucleotide sequences that are essentially the same as the that of the DNA of the source chromosome or region, and which specifically hybridize to the DNA of the chromosome or region.

It will be understood that references herein to "hybridizing a probe or paint to a chromosome," and the like, refer to hybridization or annealing of nucleic acid probes to the DNA of the target chromosome.

II. Cross-Species Color Banding Probes

Cross-species color banding (CSC-banding) entails the hybridization of detectably labeled probes (CSC-banding probes) derived from the nucleic acids of one or more species, to the chromosomes (e.g., metaphase spreads) of a different species. The chromosome(s) from which the probes are derived are sometimes referred to as the "source chromosome(s)". The chromosome or chromosomes to which the detectably labeled probes are hybridized are sometimes referred to as "target" chromosomes.

Production of CSC-banding probes involves (1) selection of one or more species from which to make chromosome-specific or subchromosome-region specific probes, (2) isolation of chromosomes and differential labeling of the chromosome-specific probes derived from the chromosomes, and (3) combining two or more chromosome specific probes derived from chromosomes of one or more species to produce the CSC-banding probes of the invention.

CSC-banding can be carried out using probes and target chromosomes from any suitable combinations of species. For the sake of clarity, however, the following description focuses largely on the use of CSC-banding probes derived from nucleic acids of one or more non-human species to detect a chromosomal aberration(s) in target chromosomes from a human. It will be appreciated that this is not intended to limit the scope of the invention.

A. Source Chromosomes for CSC-Banding Probes

The CSC-banding probes of the invention are made from DNA sources other than that of the target chromosomes. Thus, when the goal is to detect a chromosomal abnormality in a human chromosome or karyotype, the CSC-banding probes are made from DNA from a non-human species, such as a non-human animal (e.g., a non-human vertebrate). The probes from the non-human chromosome will hybridize to corresponding (homologous) non-repetitive sequences in the human chromosomes. Importantly, many non-human chromosomes exhibit rearrangements of chromosomal regions relative to the homologous regions of human chromosomes. Thus, when DNA probes from a particular non-human chromosome are uniformly labeled and hybridized to one or more human chromosomes, a non-uniform pattern of hybridization will result (reflecting the pattern of rearrangements), thus allowing a practitioner to distinguish between different regions of the target chromosome. Put differently, a chromosome specific paint from a non-human species chromosome that exhibits rearrangements relative to human chromosome will, when hybridized to the human karyotype, produce a banding pattern in the human chromosomes.

A uniformly labeled probe from a single chromosome provides limited resolution of the structure of the human chromosome(s), however, and is of limited utility for diagnosis or prognosis of human diseases. Resolution is considerably improved by using a mixture of chromosome-specific probes derived from several different chromosomes, at least some of which are differently labeled. Two chromosome-specific probes are differently labeled relative to each other when they carry distinguishable detectable labels, different combinations of detectable labels, different ratios of detectable labels, or otherwise can be distinguished (e.g., due to emission of different spectra) after hybridization to the target chromosome(s). Differential labeling techniques are well known in the art (e.g., Speicher et al., 1996, *Nature Genet.* 12:368–75) and are further described infra.

Thus, in one embodiment, chromosome-specific probes corresponding to each chromosome of a non-human species are labeled with a distinct detectable label and used for CSC-banding to human chromosomes. More often, less than the complete set of chromosomes from the non-human species will be used, and two or more chromosomes may carry the same detectable label.

Provided with particular target chromosomes (e.g., the human karyotype), the selection of particular combinations of chromosomes (e.g., non-human chromosomes) from which to make suitable chromosome-specific probes, the combination of chromosome-specific probes, and the selection of particular detectable labels will depend on the degree of resolution desired by the practitioner. Suitable combinations of non-human chromosomes from which to make chromosome-specific probes can be identified according to the teaching of Examples I and II, infra. Typically, in the case of human target chromosomes, suitable probe chromosomes are identified by:

(1) Isolating chromosomes from the non-human species (e.g., using flow cytometric methods as described infra);

(2) Making detectably labeled probes from each isolated chromosome (e.g., using DOP-PCR as described infra);

(3) Hybridizing the labeled probes to the human karyotype to identify regions of homology (e.g., as using standard in situ hybridization techniques, as described infra);

(4) Mapping regions of homology between the target karyotype and the chromosomes or karyotype and the source chromosomes;

(5) Identifying which bands on the human karyotype correspond to each non-human chromosome-specific probe; and, (6) Selecting combinations of chromosome-specific probes to provide the desired number (e.g., usually at least 40) and distribution of bands on the target chromosomes.

Combinations of chromosome-specific probes are selected for pooling to make the CSC-banding probes of the invention such that several different segments or regions of the target (e.g., human) chromosomes are delineated (assuming that each chromosome-specific probe is differently labeled). Typically at least about 40 different segments are delineated, more often at least about 70, still more often at least about 80, and very often at least about 90 or more different segments of the target chromosome (e.g., human karyotype) are delineated. It will be recognized that a more detailed banding pattern provides higher levels of resolution and facilitates the identification of chromosome abnormalities.

In one embodiment of the invention, the CSC-banding probes contain chromosome-specific probes derived from one nonhuman species (e.g., *H. concolor*); in alternative embodiments, chromosome-specific probes derived from more than one non-human species can be combined, as described in Example II, infra, to increase the resolution (number of distinguishable bands) upon hybridization of the CSC-banding probes to the target chromosomes. Thus, in various embodiments, the CSC-banding probes of the invention comprise a mixture of nucleic acids, or chromosome-specific probes from more than one, e.g., 2, 3, 4 or more, different species, each of which is different from the species of the target chromosomes (e.g., non-human species when the target chromosomes are human).

When the target chromosomes are human, suitable non-human animals for generating CSC-banding probes include non-human primates, other mammals, reptiles, amphibians, birds, and fish. In one embodiment, the non-human animal is a non-human primate such as an ape (i.e., from subfamily Hylobatinae or Ponginae), for example a gibbon (genus Hylobates), orangutans (genus Pongo), chimpanzee (genus Pan, e.g., Pan troglodytes), and/or gorilla (genus Gorilla). In another embodiment, the non-human animal is an Old World monkey (i.e., family Cercopithecidae such as baboons, mandrills, macaques, guenons, mangabeys, langurs, guerezas, and African Green monkey (*Cercopithecus aethiops*), or a New World monkey such as marmosets, howler monkeys, spider monkeys, capuchins, owl monkeys, and woolly spider monkeys, and others.

Non-human primates are especially good sources of CSC-banding probes because (1) they share with humans a high level of conservation in coding sequences and a high level of divergence in non-coding sequences and, (2) many show numerous rearrangements relative to humans. For example, the karyotypes of gibbons (e.g., *H. hoolock*, 2n=38; *H. lar*, 2n=44; *H. syndactylus*, 2n=50 and *H. concolor*, 2n=52) show extensive chromosomal reorganization (e.g., translocations) when compared to human chromosomes. Another example of suitable non-human primates are the *Cercopithecus monkeys*, in which chromosome fissions predominate (karyotypes vary from 2n=48 to 72; see, Dutrillaux et al., 1979, *Hum. Genet.* 48:251–314). Thus, probes derived from the chromosomes of these species are particularly useful for generating chromosome arm specific probes for human karyotype analysis.

As noted supra, in some embodiments chromosome-specific probes from two or more species are combined in the CSC-paints to provide additional resolution. Thus, in one embodiment the CSC-banding probes are a mixture of *Hylobates concolor* and *H. syndactylus* sequences.

B. Isolation of Specific Chromosomal Sequences

To prepare chromosome-specific probes that are distinctly labeled, it is necessary to isolate DNA from the chromosome (s) to be labeled in one way from the DNA of the other chromosomes (i.e., those to remain unlabeled or to be differently labeled). In one embodiment of the invention, individual chromosomes are isolated by flow cytometry using well established methods (see, e.g., Collins et al., 1991, *Genomics* 11:997–1006; Rabbitts et al., 1995, *Nat. Genet.* 9:369–75; and Ferguson-Smith, 1997, *Europ. J. Hum.Genet.* 5:253–65).

In other embodiments, the chromosomes may be physically separated, fragmented, and the fragments propagated as clones, as in Van Dilla, et al., 1986, *Bio/Technology* 4:537–52, and Cox et al., 1990, *Science* 250: 245–50. Alternatively an entire chromosome may be physically scraped from the surface of a microscope slide, fragmented, and the fragments propagated as clones (Ludeck et al., 1989, *Nature* 338:348–50) or microdissected fragments of chromosomes may be used (see, e.g., Trautman et al., 1991, *Hum. Genet.* 87:495–97). Single chromosomes from a particular species may also be propagated in somatic cell hybrids, and the sequences of the chromosome of interest amplified using species-specific PCR primers (e.g., utilizing primer oligonucleotides complementary to abundant, polydisperse repeated DNA sequences which present in the target chromosomes but not the chromosomes of the host cell (see, e.g., Nelson et al., 1989, *Proc. Natl. Acad. Sci. USA* 86:6686–90, describing the amplification of human sequences from human-rodent cell hybrids using Alu-specific primers). It will be recognized that the particular method of separating chromosomes of interest from others is not critical to the invention, and that other methods may be used.

Following isolation or purification of specific chromosome preparations (e.g., containing one or a few chromosomes), chromosome-specific probes may be produced from chromosomal DNA using enzymatic amplification methods such as the polymerase chain reaction (e.g., degenerate oligonucleotide primed-PCR; Telenius et al., 1992, *Genes, Chromosomes & Cancer* 4:257–63). Once a set of amplified nucleic acid probes (e.g., DOP-PCR fragments) is produced, the probes may be re-amplified. Typically, the probes (e.g., preferably ranging from about 400 to about 1000 bases in length) are labeled during the re-amplification step.

C. Labeling CSC-Banding Probes

1. Method of Labeling

The chromosome-specific probes used in the CSC-banding probes of the invention are labeled with one or a combination of detectable labels (e.g., the probe may be directly labeled, indirectly labeled, or both). Methods for incorporating detectable labels into nucleic acid probes are well known. Typically, detectable labels (e.g., as hapten- or fluorochrome-conjugated deoxyribonucleotides) are incorporated into a polynucleotide probe during a polymerization or amplification step, e.g., by PCR, nick translation, random primer labeling, terminal transferase tailing, and others (see Ausubel et al., 1997, CURRENT PROTOCOLS IN MOLECULAR BIOLOGY, Greene Publishing and Wiley-Interscience, New York). A preferred method for generating the labeled CSC-banding probes of the invention is by degenerate oligonucleotide primed-PCR (DOP-PCR) in the presence of a labeled dNTP (e.g., Cy3-dUTP). See, Telenius et al., 1992, supra. According to this method, a degenerate PCR primer is used for essentially random amplification of target DNA from any source. As noted supra, the detectably labeled chromosome-specific probes of the invention are typically generated by re-amplification of isolated chromosome-specific nucleic acids.

In one embodiment, the probes of the invention are fluorescently labeled. Suitable fluorochromes for labeling include fluorescein-isothiocyanate [FITC] (e.g., FITC-dUTP); cyanine dyes, e.g., Cy3 (e.g., Cy3-dUTP), Cy2, Cy3.5, Cy5, Cy5.5, Cy7 [Amersham]; fluorescein, Texas red, rhodamine, lissamine, phycoerythrin, FluorX [Amersham], SyBR Green I & II [Molecular Probes], Spectrum Green (e.g., Spectrum-Green-dUTP), Spectrum Orange, and the like. Examples of indirect labels which may be used to for detection include haptens such as biotin (e.g., biotin-dUTP); digoxigenin (e.g., digoxigenin-dUTP), and fluorescein-isothiocyanate. Haptens may be detected following the hybridization of the CSC-banding probe to the target chromosomes using a labeled anti-hapten. For example, avidin is used to detect biotin-labeled probes (e.g., avidin-Cy-5 [Amersham], avidin-FITC, avidin-Cy-3); digoxigenin is detected with anti-digoxigenin antibody (e.g., FITC conjugated-anti-digoxigenin antibody; rhodamine-anti-digoxigenin antibody, unlabeled rabbit anti-FITC primary antibody detected using FITC-conjugated goat anti-rabbit secondary antibody), and the like. Numerous labeling systems will be apparent to those of skill in the art.

When a given probe (e.g., a chromosome-specific probe) is labeled with more than one label, this may be accomplished by, for example, amplifying the probe in the presence of more than one labeled nucleotide (e.g., DOP-PCR in the presence of Cy3-dUTP and FITC-dATP). More often, however, labeling will be accomplished by dividing the chromosome specific probe into multiple (e.g., 2) portions, labeling one portion with one label (e.g., DOP-PCR in the presence of Cy3-dUTP), labeling the other portion with a different label (e.g., DOP-PCR in the presence of FITC-dATP), and combining the two labeling reactions to produce a multiply-labeled probe.

2. Combinatorial Multi-Color FISH

As noted supra, the CSC-banding probes of the invention include multiple chromosome-specific probes (e.g., from non-human chromosomes), which are differentially labeled (i.e., at least two of the chromosome-specific probes are differently labeled). This permits the identification of numerous chromosome subregions in a single FISH experiment. In one embodiment, each chromosome from a non-human primate is used to prepare a uniquely labeled chromosome-specific probe, with each probe producing a distinct color when hybridized to the target chromosomes (and appropriately treated, e.g., by adding an avidin-fluorochrome conjugate to hybridized probes comprising a biotin label). As noted supra, and as illustrated in the Examples below, more often, less than the complete set of chromosomes from a particular non-human species will be used, and two or more chromosomes may carry the same detectable label. In addition to the methods illustrated in the Examples, various approaches to multi-color chromosome painting have been described in the art and can be adapted to the present invention following the guidance provided herein. Examples of such differential labeling ("multicolor FISH") include those described by Schröck et al., 1996, Science 273:494–97 and Speicher et al., 1996, Nature Genet. 12:368–75). Schröck et al., supra, describe a spectral imagining method, in which epifluorescence filter sets and computer software is used to detect and discriminate between multiple differently labeled DNA probes hybridized simultaneously to a target chromosome set. Speicher et al., supra, describe using different combinations of 5 flurochromes to label each of the human chromosomes (or chromosome arms) in a 27-color FISH termed "combinatorial multifluor FISH"). Other suitable methods may also be used (see, e.g., Ried et al., 1992, Proc. Natl. Acad. Sci. USA 89:1388–92).

It will be recognized by those of skill that the color resolution of the CSC-banding pattern depends, in part, on the number of labels or haptens used. Using three haptens simplifies the analysis of the CSC-banding pattern since the probes can be displayed in a simple red/green/blue (RGB) format accessible to most fluorescence microscopes and custom image processing computer software (Nederlof et al., 1990, Cytometry 11:126–31; Ried et al., 1992, Proc. Natl. Acad. Sci. USA 89:1388–92). However, this arrangement does reduce the possibility of identifying small telomeric transpositions due to redundancy in the color assignment.

III. In situ Hybridization

Hybridization of the CSC-banding probes of the invention to target chromosomes sequences (e.g., metaphase spreads) is accomplished by standard in situ hybridization (ISH) techniques (see, e.g., Gall and Pardue, 1981, Meth. Enzym. 21:470–80; Henderson, 1982, Int. Review of Cytology 76:1–46). Generally in situ hybridization comprises the following major steps: (1) fixation of the biological structure to be analyzed (e.g., a metaphase chromosome spread), (2) prehybridization treatment of the biological structure to increase accessibility of target DNA (e.g., denaturation with heat or alkali), (3) optionally prehybridization treatment to reduce nonspecific binding (e.g., by blocking the hybridization capacity of repetitive sequences, e.g., using human genomic DNA), (4) hybridization of the mixture of nucleic acids to the nucleic acid in the biological structure or tissue; (5) posthybridization washes to remove nucleic acid fragments not bound in the hybridization and (6) detection of the hybridized nucleic acid fragments. The reagents used in each of these steps and their conditions of use vary depending on the particular situation. An exemplary protocol for hybridization of CSC-banding probes is provided in Example III, infra. Hybridization conditions are also described in U.S. Pat. No. 5,447,841. It will be appreciated that numerous variations of in situ hybridization protocols and conditions are known and may be used in conjunction with the present invention by practitioners following the guidance provided herein.

Conventionally, hybridization of chromosome paints to chromosomes is carried out using a blocking step, e.g., prehybridization with unlabeled competitor DNA (e.g., Cot-1 DNA). Hybridization in the absence of competitor DNA, but using a preannealing step, has been described by Wienberg et al., 1997, supra. When these methods are used, background (cross-hybridization) is observed for probes derived from certain chromosomes (e.g., 13 and 21). However, when the CSC-banding probes of the invention are used, no Cot-1 DNA or preannealing step is required, and cross-hybridization is minimal for all chromosomes. Without being bound by a particular mechanism, it is believed that the primary factor contributing to the absence of background cross hybridization when CSC-banding probes from non-human primates are used in the absence of competitor DNA, is the higher evolutionary sequence divergence and higher variation in copy numbers and chromosomal location of repetitive DNA compared to highly conserved single copy DNA among animal species.

The in situ hybridization methods of the invention for detecting chromosomal abnormalities (e.g., FISH) disclosed herein can be performed on a variety of biological or clinical samples, in cells in mitosis and meiosis or in interphase cells. Examples include all types of cell culture, peripheral blood lymphocytes, buccal smears, touch preparations prepared from uncultured primary tumors, cancer cells, bone marrow, cells obtained from aspiration biopsy or cells in bodily fluids (e.g., blood, urine, sputum and the like), cells from amniotic fluid, cells from maternal blood (e.g., fetal cells), cells from testis and ovary, and the like.

IV. Detection and Image Analysis

The detection method(s) used will depend on the particular detectable labels used in the CSC-banding probe. When fluorescently labeled CSC-banding probes are used fluorescence photomicroscopy can be used to detect and record the results of in situ hybridization, using routine methods known in the art. Alternatively, digital (computer implemented) fluorescence microscopy with image-processing capability may be used.

In one embodiment, images of the fluorescently labeled chromosomes are detected and recorded using a computerized imaging system such as the Applied Imaging Corporation CytoVision System (Applied Imaging Corporation, Santa Clara, Calif.) with modifications (e.g., software, Chroma 84000 filter set, and an enhanced filter wheel). Other suitable systems include a computerized imaging system using a cooled CCD camera (Photometrics, NU200 series equipped with Kodak KAF 1400 CCD) coupled to a Zeiss Axiophot microscope, with images processed as described by Ried et al., 1992, *Proc. Natl. Acad. Sci. USA* 89:1388–92). Other suitable imaging and analysis systems are described by Schröck et al., 1996, *Science* 273:494–97; and Speicher et al., 1996, *Nature Genet.* 12:368–75.

V. Kits

The CSC-banding probes of the invention are conveniently provided in kit form. In one embodiment, the kit comprises a container including one or more of:

(a) at least one vial or container comprising chromosome-specific probes (e.g., painting probes) from a non-human animal (e.g., a non-human primate); the probes may be either detectably labeled or not labeled;

(b) at least one vial or container comprising chromosome-specific probes (e.g., painting probes), which may be labeled or unlabeled, from two or more different non-human animal (e.g., two or more different non-human primates);

(c) at least one vial or container comprising chromosome-specific probes from one or more human chromosomes;

(d) at least one vial or container as described in (a)–(c) supra, further comprising formnamide;

(e) at least one vial or container as described in (a)–(d), supra, further comprising NaCl and/or sodium citrate;

(f) a separate vial comprising at least one of the following reagents: formamide, 4,6-diamidino-2-phenylindole (DAPI), an anti-hapten antibody (e.g., anti-FITC antibody), a detectably labeled secondary antibody to the anti-hapten (e.g., anti-FITC) antibody, fluorochrome-conjugated avidin, an fluorescence antifade reagent (e.g. Citifluor or Vectasheild);

(g) printed instructions for detecting a chromosomal aberration in a human chromosome by CSC-banding;

(h) a photograph or drawing of a normal human karyotype stained with the probes provided in the kit (or their equivalent);

It will be apparent to those of skill that numerous other reagents or compositions, and combinations of reagents or compositions may be provided in kit form.

VI. EXAMPLES

The following examples are intended to illustrate the invention, and not to limit it in any manner.

Example I

Metaphase spreads from peripheral blood lymphocytes and lymphoblastoid cell lines were prepared and blood samples were obtained from a normal human male and from clinical cases showing chromosome abnormalities. A lymphoblastoid cell line was obtained from a male Concolor gibbon (*Hylobates concolor*, 2n=52). Flow sorting of concolor gibbon (HCO) chromosomes was performed on a dual laser cell sorter (FACStar Plus, Becton Dickinson Immuno-Cytometry Systems). Bivariate flow cytometry yielded 25 peaks which were identified by comparison of their hybridization patterns to homologies revealed by human chromosome specific paints on HCO chromosomes. This revealed that single chromosome-specific paints could be obtained from 17 chromosomes (Table 1). Four peaks contained two chromosomes (HCO X+5, HCO 9+11, HCO 12+15, and HCO 6+7). Chromosome numbering followed that of Koehler et al., 1995, *Genomics* 30:287–92. Three hundred to five hundred chromosomes of each type were amplified by a preliminary round of DOP-PCR followed by a secondary amplification incorporating labeled-dUTP as described in Telenius et al., 1992, *Genes, Chromosome & Cancer* 4:257–263.

The probe-labeling scheme for generating the fluorescent probes used in the multicolor experiments is shown in Table 1, infra. (Examples of alternative labeling schemes are shown in Tables 2 and 3, infra.) In this example three labels were used namely, Cy-3, FITC and biotin. Hybridization and detection were carried out using a modification of the procedure described by Pinkel et al., 1988, *Proc. Nat'l. Acad. Sci. USA* 85:9138–42. However, all hybridizations were performed in the absence of unlabeled competitor DNA (e.g. Cot-1 DNA). Multicolor in situ hybridization experiments required 150 ng of each DNA probe, precipitated in ethanol and resuspended in 15 µl of hybridization buffer. DNA probes were denatured at 68° C. for 7 minutes and pre-annealed by incubation at 37° C. for 30 minutes. The chromosome preparations were denatured in 70% formamide/2×SSC at 68° C. for 1 minute and hybridized overnight with the DNA probe mixture at 37° C. Post hybridization washes included 2×5 minutes in 50% formamide/1×SSC at 45° C. and 2×5 minutes in 2×SSC at 45° C. Biotinylated probes were detected by avidin-Cy5. Metaphases were analyzed with the cooled CCD camera (Photometrics NU200 equipped with a KAF1400 chip) coupled to a fluorescence microscope. Camera control and digital image acquisition was as described by Ried et al., 1992, *Proc. Nat'l Acad. Sci. USA* 89:1388–92. Merging of chromosome images was performed using Adobe PhotoShop 3.0 software.

Figure 1:
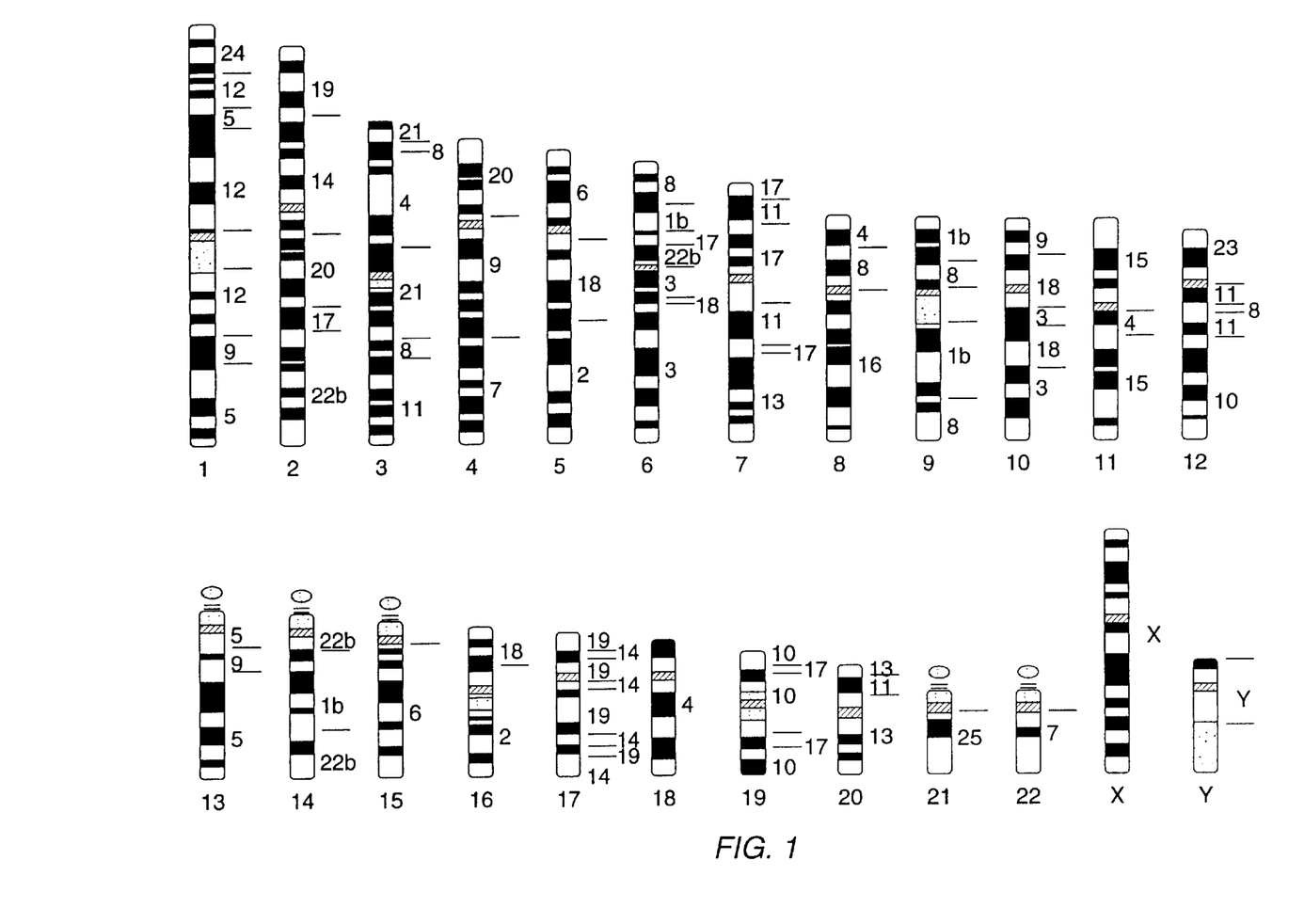
FIG. 1 shows an idiogram summarizing in situ hybridization to human chromosomes by chromosome specific probes from *H. concolor*.

When the HCO chromosome specific paint mixture was hybridized to a sample of normal human metaphases, the chromosome complement was differentiated into 80 separately colored segments, consistent with previous single chromosome painting experiments using human chromosome specific paints on gibbon chromosomes (Koehler et al., 1995, supra). The hybridization efficiency and reproducibility were comparable with that of human specific paints. Apart from the human chromosome regions 4q27-qter, 22q and the Y chromosome (homologous to gibbon chromosome 7 and Y which were not represented in the probe mixture in this example), human euchromatic regions were painted in their entirety by the HCO chromosome specific paint mixture (FIG. 1.) The HCO paints did not cross-hybridize with heterochromatic regions of different human chromosomes.

Figure 2:
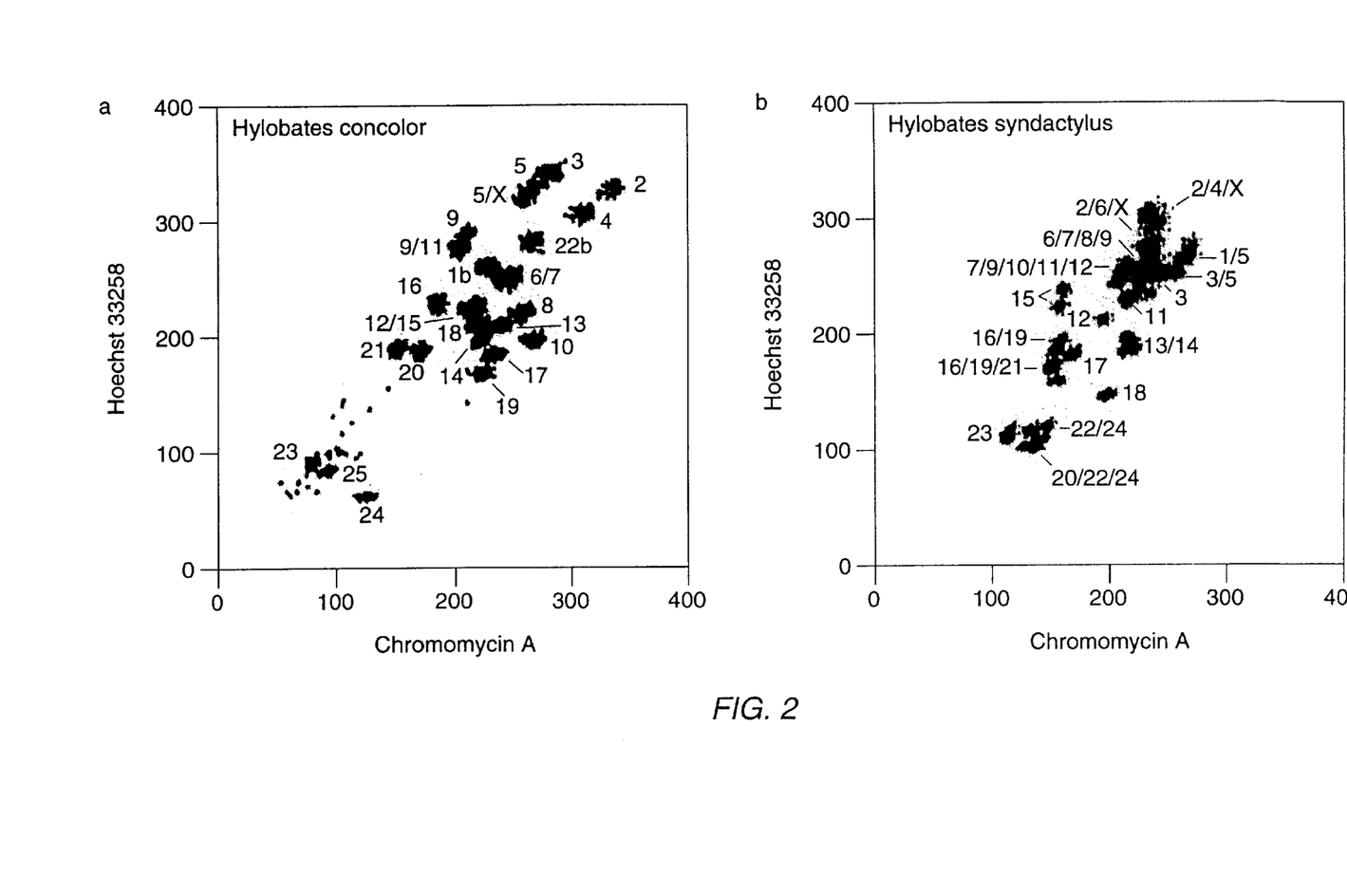
FIG. 2 shows bivariate flow karyotypes of (a) male *Hylobates concolor* and (b) female *H. syndactylus* chromosomes from lymphoblastoid cell cultures. Probes established by degenerate oligonucleotide primed-PCR (DOP-PCR) from flow sorted chromosomes and in situ hybridization of these probes to gibbon metaphase spreads allowed the chromosomal assignment of each peak. Chromosome numbering followed Koehler et al., 1995, *Genomics*, 30:287–292 and Koehler et al., 1995, *Am. J. Phys. Anthropol.*, 97:37–47. For the male *H. concolor*, a Y chromosome was sorted from close to the debris spike (not shown).

With the exception of human chromosomes 15, 18, 21, 22 and the X, every human chromosome was painted by more than one and up to six different gibbon chromosomes. Additionally, 9 human chromosomes (1, 3, 7, 9, 10, 11, 14, 17 and 19) showed two or more signals derived from one gibbon chromosome. This indicates the occurrence of inversions as well as translocations during divergence of the human and gibbon species.

were hybridized to the DAPI banded chromosomes of the particular species. FIG. 2 shows the flow karyotype of the two species. Many peaks contained single chromosomes only, however, especially in *H. syndactylus*, a number of chromosomes could not be resolved individually, resulting in composite probes. The Gibbon probes derived from the primary reaction and the same primers were used to label the chromosome paints with one or more of biotin-dUTP (Vector Laboratories), FITC-dUTP (Amersham), and Cy3-dUTP (Amersham), as shown in Table 4, in 50 μl standard DOP-PCR reactions (Rabbitts et al., supra).

TABLE 1

Labeling Scheme for Gibbon Chromosome-Specific Probes

| Chromosome | 1b | 2 | 3 | 4 | 5 | 5/x | 6 + 7 | 8 | 9 | 9/11 | 10 | 12/15 |
|---|---|---|---|---|---|---|---|---|---|---|---|---|
| Cy3 |  |  | x |  |  |  | x | x |  |  |  |  |
| Biotin | x | x |  | x | x |  |  |  | x |  | x |  |
| FITC |  |  |  | x |  |  | x | x |  | x |  | x |

| Chromosome | 13 | 14 | 16 | 17 | 18 | 19 | 20 | 21 | 22b | 23 | 24 | 25 |
|---|---|---|---|---|---|---|---|---|---|---|---|---|
| Cy3 | x | x | x |  |  |  | x |  | x |  |  | x |
| Biotin | x |  |  | x | x | x | x | x |  | x |  |  |
| FITC | x |  |  | x | x | x | x |  |  |  | x | x |

TABLE 2

Labeling Scheme for Gibbon Chromosome-Specific Probes

| Chromosome | 1b | 2 | 3 | 4 | 5/X | 6/7 | 8 | 9 | 10 | 11 | 12/15 |
|---|---|---|---|---|---|---|---|---|---|---|---|
| FITC |  |  | x |  | x | x | x |  |  |  |  |
| Cy3 | x |  |  | x |  |  |  | x | x |  |  |
| Cy5 |  | x |  | x |  | x |  |  |  | x | x |

| Chromosome | 13 | 14 | 16 | 17 | 18 | 19 | 20 | 21 | 22b | 23 | 24 | 25 | Y |
|---|---|---|---|---|---|---|---|---|---|---|---|---|---|
| FITC | x | x | x |  |  | x |  | x |  |  | x | x |  |
| Cy3 | x |  | x | x | x | x | x | x |  |  | x | x |  |
| Cy5 | x |  |  | x | x | x | x |  | x |  | x |  |  |

TABLE 3

Labeling Scheme for Gibbon Chromosome-Specific Probes

| Chromosome | 1b | 2 | 3 | 4 | 5/X | 6/7 | 8 | 9 | 10 | 11 | 12/15 |
|---|---|---|---|---|---|---|---|---|---|---|---|
| FITC | x | x |  | x | x | x |  |  |  |  |  |
| Cy3 | x |  |  | x |  |  |  | x | x |  |  |
| Cy5 |  |  |  | x |  | x |  |  |  | x | x |

| Chromosome | 13 | 14 | 16 | 17 | 18 | 19 | 20 | 21 | 22b | 23 | 24 | 25 | Y |
|---|---|---|---|---|---|---|---|---|---|---|---|---|---|
| FITC | x | x | x | x | x | x |  | x |  |  | x | x | x |
| Cy3 | x |  | x | x | x | x | x | x |  |  | x | x |  |
| Cy5 | x |  |  |  | x | x |  | x |  | x |  |  |  |

Example II a) Preparation and Characterization of Chromosome-Specific Probes Using FACS and subsequent DOP-PCR, chromosome-specific probes from *Hylobates concolor* and *H. syndactylus* chromosomes were prepared. Briefly, gibbon chromosomes were sorted using a dual laser flow sorting system as described for other species (Rabbitts et al., 1995, *Nature Genet.* 9:369–75; Ferguson-Smith, 1997, *Europ. J. Hum. Genet.* 5:253–65) Chromosome specific probes were generated by degenerate oligonucleotide primed PCR (DOP-PCR) directly from the flow sorted chromosomes using PCR primers and amplification conditions as described (Telenius et al., 1992, *Genes, Chromosomes Cancer* 4:257–63).

To identify the content of each peak in the flow karyotype, hapten labeled probes derived from the individual peaks

TABLE 4

Fluorescence Labeling Scheme for Gibbon Chromosome Specific Probes
(HCO = *Hylobates concolor*, HSY = *H. syndactylus*)

| Biotin (Cy-5) | FITC-dUTP | Cy3-dUTP |
|---|---|---|
| HCO 2 | HCO 8 | HCO 1b |
| HCO 3 | HCO 12 | HCO 4 |
| HCO 5 | HCO 15 | HCO 8 |
| HCO 6 | HCO 17 | HCO 9 |
| HCO 7 | HCO 18 | HCO 13 |
| HCO 11 | HCO 19 | HCO 14 |
| HCO 12 | HCO 20 | HCO 16 |
| HCO 15 | HCO 22b | HCO 18 |
| HCO 16 | HCO 25 | HSY 13 + 14 |
| HCO 17 | HSY 3 | HSY 22 + 24 |
| HCO 21 | HSY 12 |  |
| HCO 23 | HSY 15 |  |
| HCO 24 | HSY 17 |  |
| HCO X |  |  |

In situ hybridization of probes to human and gibbon chromosomes was performed as previously described (Rabbitts et al., 1995, supra). No Cot-1 DNA for suppression was necessary, both for the hybridizations of gibbon probes on gibbon chromosomes and gibbon on human chromosomes. The chromosome paints labeled with biotin were detected with avidin-Cy-5 (Amersham).

Digital images were obtained using a cooled CCD camera (Photometrics, NU200 series equipped with Kodak KAF 1400 CCD) coupled to a Zeiss Axiophot microscope. Camera control and digital image acquisition (8-bit grey scale) employed an Apple Macintosh computer. The images were processed as described (Ried et al., 1992, *Proc. Natl. Acad. Sci. USA* 89:1388–92). Photographs from the images were taken directly from the computer. At least ten metaphases were evaluated for each painted chromosome to define the areas hybridized by any particular probe.

Figure 3:
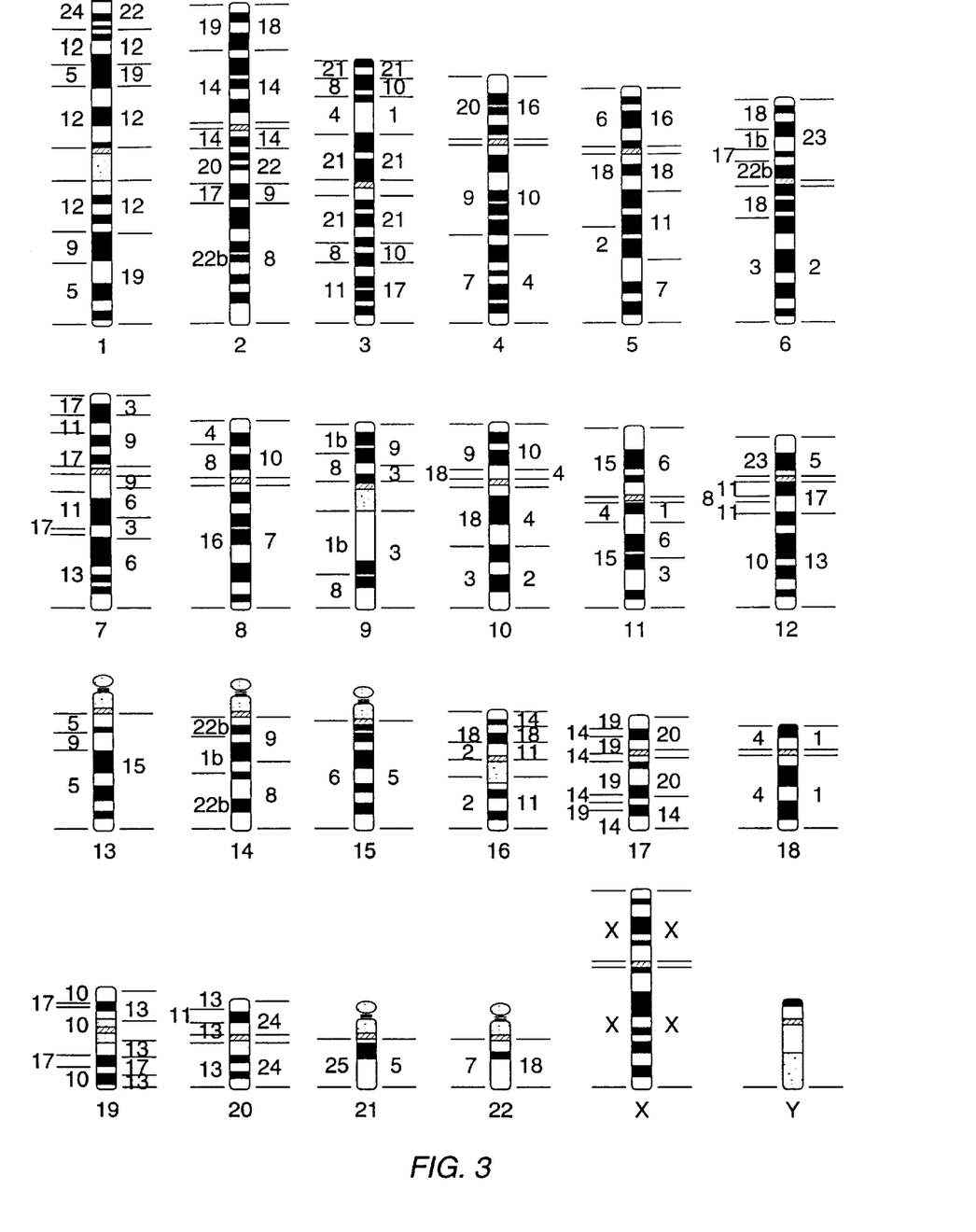
FIG. 3 shows an idiogram summarizing in situ hybridization experiments painting human chromosomes with chromosome specific probes derived from two different gibbon species (*H. concolor* and *H. syndactylus*). The hybridization sites and the number of the gibbon painting probes are given on the left side of each chromosome for the *H. concolor* gibbon and on the right side for the *H. syndactylus* gibbon.
Figure 4:
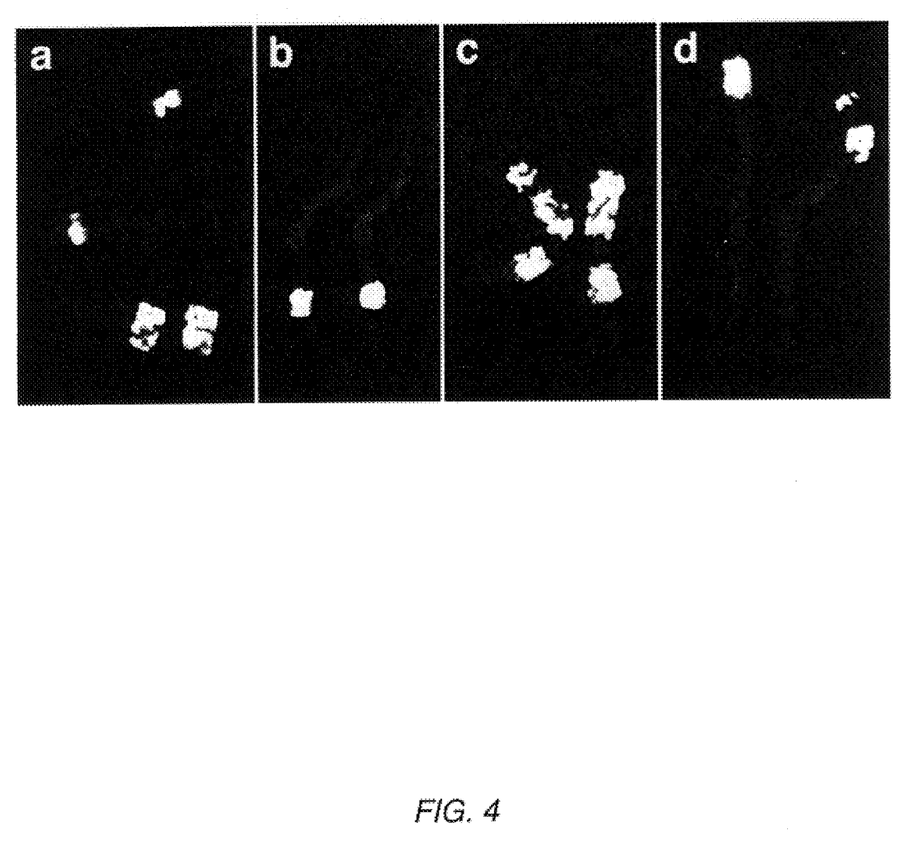
FIG. 4 shows various gibbon single chromosome probes delineating subregions of human chromosome 1 from a patient with a transposition (46,XY,inv(1)(p36.1;p31p32).

Hybridization of gibbon painting probes to human chromosomes showed that, with the exception of human chromosomes 15, 18, 21, 22 and the sex chromosomes, each chromosome was differentiated in at least two and up to six subregions. Some human chromosomes showed only poor subregional differentiation with probes derived from both species while other human chromosomes were highly differentiated. In total, the human karyotype could be differentiated into 81 homologous segments with probes derived from *H. concolor*, and 74 segments with probes derived from *H. syndactylus*. FIG. 3 gives a summary of the results in an idiogram of human chromosomes. To distinguish between identical and merely similar subregions painted by probes from different gibbon species, hybridizations were also performed between gibbons. This, for example, showed that the pattern obtained on human chromosome 19 with probes derived from both *H. concolor* and *H. syndactylus* was identical (FIG. 3), whereas on human chromosome 17 the hybridization between the two gibbons clearly indicated different rearrangements.

b) Use of Gibbon Chromosome Specific Probes to Identify Human Chromosome Aberrations Gibbon chromosome specific paints were applied as diagnostic tools in various patients to identify chromosome rearrangements, including inversions, transpositions, transpositions and aneuploidies. In one of the patients, *H. concolor* painting probes identified a rearrangement within chromosome 1 (FIG. 4). The results indicate a transposition of chromosome 1 p31 p32 material into band 1 p36.1. Remarkably, the deletion breakpoints both in 1 p31 and 1 p32 coincide with the boundaries of *H. concolor* chromosome 5 material homologous to this region, indicating similar breakpoints both in gibbon chromosome evolution and in human pathology.

c) Use of CSC-Banding Probes for Karyotype Analysis

Gibbon chromosome-specific paints were not only used in single hybridization experiments, but also in pools containing combinatorially labeled probes from individual species. In a single experiment the entire human karyotype was delineated in a multicolor format which resulted in a banding pattern (i.e., cross-species-color-banding). In these experiments, single gibbon paints were pooled into three probe sets (as in Tables 1–3) labeled with either Cy-3-dUTP, FITC-dUTP, biotin-dUTP (detected with AvidinCy-5), or Cy5-dUTP, and displayed false colored in red green, and blue (RGB). Four microliters (containing approximately 300 ng) of each individual Gibbon probe was pooled, ethanol precipitated, and resuspended in 15 $\mu$l of 50% formamide, 2×SSC, 10% dextran sulfate. The Boolean combination of these probe pools (Nederlof et al., 1990, *Cytometry* 11:126–31; Ried et al., 1992, *Proc. Natl. Acad. Sci. USA* 89:1388–92) resulted in a seven color CSC-banding pattern. Regions of the human karyotype to which chromosome-specific probes present in only one pool hybridized, appeared either red, green or blue; regions to which chromosome-specific probes from more than one pool hybridized exhibited defined mixed colors of the RGB-spectrum. Each human chromosome exhibited a unique banding pattern which was different for the probe set derived from the two gibbon species. The CSC-banding pattern observed corresponded with that expected from the painting data using individual probes (FIG. 3).

Figure 5:
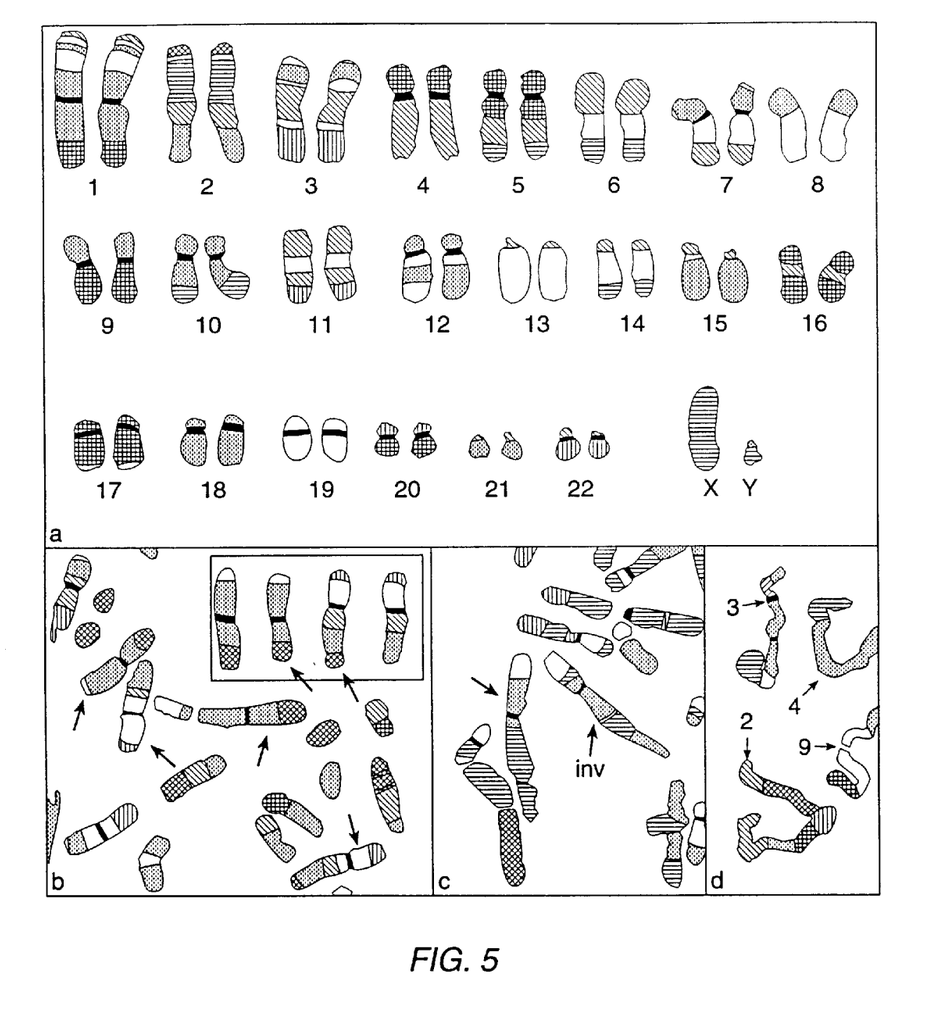
FIG. 5 shows cross-species color banding (CSC-banding) using gibbon chromosome specific paints on human chromosomes. (a) karyotype of normal human chromosomes using the probe set derived from *H. syndactylus*. (b)–(c) Chromosome rearrangements from patients delineated by CSC-banding: (b) CSC-banding with the *H. syndactylus* (Siamang) probe set showing a metaphase with a translocation (t(1;2)(q37;q42.3)). In the metaphase, chromosomes 1 and 2 are marked by arrowheads. In the box, rearranged chromosomes are indicated by arrows; (c) CSC-banding with the probe set derived from the *H. concolor* (Concolor) gibbon showing a metaphase with a pericentric inversion on chromosome 2 (inv(2)(p23q13). The normal chromosome is indicated with an arrowhead while the aberrant chromosome is marked by an arrow; (d) Selected prophase chromosomes from a hybridization with a different color combination used for chromosome labeling.

FIG. 5a shows a human karyotype stained using probes made from *H. syndactylus* chromosomes. No chromosome aberrations were detected in this karyotype. Clinical cases analyzed with the CSC-banding are shown in FIGS. 5b and 5c. FIG. 5b shows CSC-banding with a *H. syndactylus* probe set showing a metaphase with a translocation (t(1;2) (q37;q42.3)), and 5c shows CSC-banding with a probe set derived from the *H. concolor* gibbon, showing a metaphase with a pericentric inversion on chromosome 2 (inv(2) (p23q13). An even more differentiated CSC-banding was achieved by mixing probes from the two different species (Table 4 and FIG. 3). This improved the resolution of chromosome subregions over that achieved using a single species.

Example III

This example describes the use of an *H. concolor* CSC-banding probe in human karyotyping. CSC-banding probe is prepared as described in Example I, supra, and labeled according to the scheme of Table 2. The probe is suspended, typically at a concentration of about 10–30 nanograms per microliter of each chromosome-specific probe, in formamide hybridization buffer (50% formamide, 10% dextran sulfate, 2×SSC, 40 mM NaPO4 (pH 7), 1×Denhardt's Solution (Ausubel et al., 1997, CURRENT PROTOCOLS IN MOLECULAR BIOLOGY, Greene Publishing and Wiley-Interscience, New York), 120 ng/$\mu$l salmon sperm DNA).

Metaphase preparations are prepared from a human lymphocyte cell culture using standard methods. The cell suspension is gently mixed and a drop applied to the slide by dropping from approximately one-inch above the slide. A drop of freshly prepared 4° C. fixative methanol: glacial acetic acid (3:1) is added and the slide is allowed to air dry. Following examination of the metaphases under phase contrast microscope, the slides are allowed to air-dry overnight at room temperature.

The slides are incubated in a 65° C. oven for 1 hr before hybridization. They are then dehydrated in 100% ethanol for 5 min and allowed to air dry. To denature the chromosomes, the slides are incubated in a Coplin jar containing Denaturation Solution at 65° C. for 90 seconds. Denaturation solution is made by mixing 5 ml 20×SSC, 10 ml purified water and 35 ml formamide, and adjusting the pH to 7.0. The slides are then quenched by immersion in ice-cold, 70% ethanol for 2 min. The samples are dehydrated in an ethanol series (70, 70, 90, 90, 100% ethanol, 2 min each).

To denature the CSC-banding probe, it is warmed at 37° C. for 5 min, mixed by gentle vortexing, and centrifugal. 12 $\mu$l of probe are transferred to a 0.5 $\mu$l microcentrifuge tube and denatured by incubating at 65° C. for 10 min. The denatured probe is transferred to 37° C. and used within 2 hr. The denatured probe is pipetted onto the slides and a 22 mm×22 mm coverslip is overlayed. The coverslip is sealed using rubber cement, and the slide is incubated overnight at 37–42° C.

Following hybridization, and without allowing the slides to dry out at any stage, the rubber cement is removed and the coverslips are floated off by incubating the slide in a Coplin jar containing 2×SSC for 5 minutes (20×SSC is made by dissolving 175.3 g of NaCl and 88.2 g of sodium citrate in 800 ml of purified water, adjusting the pH to 7.0, and adjusting the volume to 1 liter). The slides are washed 2×5 minutes at 45° C. in 50% formamide in 1×SSC, 2×5 minutes in 2×SSC at the same temperature, and incubated for 10 minutes at 45° C. in 4XT solution (4×SSC, 0.05% Tween-20).

200 $\mu$l of a 1:200 dilution in 4XT of Rabbit anti-FITC is pipetted on the slide, covered with 25 mm×40 mm Parafilm coverslip and Parafilm and incubated in a humidified chamber at 37° C. for 20–30 minutes. After washing 3×5 minutes in 4XT at 45° C, 200 $\mu$l of a 1:200 dilution of 1:100 dilution in 4XT of goat anti-rabbit FITC is added and the slide is incubated a humidified chamber at 37° C. for 20–30 minutes and washed 3×5 minutes in 4XT at 45° C. (Both immunglobulin preparations should be incubated at room temperature, centrifuged at 12,000 rpm for 10 min, and the pellet discarded prior to use.)

The slides are then incubated in 2×SSC containing 0.1 $\mu$g/ml of DAPI (4,6-diamidino-2-phenylindole) for at least 2 min, drained, mounted in mounting media (such as VectaShield), blotted, and sealed with nail polish. The FISH signals are then examined using an Applied Imaging Corporation (AIC) CytoVision System (Cat. # CKS1102 or CUS 1102) augmented with appropriate software, Chroma 84000 filter set, and an enhanced filter wheel (e.g., the AIC RxFISH CytoVision System) according to the manufacturer's instructions. The resulting karyotype is compared to that of a normal human metaphase treated with similar reagents (not necessarily concurrently) and chromosome aberrations in the subject metaphase are noted.

The present invention provides novel methods and materials relating to karyotype analysis and the diagnosis and treatment of diseases. While specific examples have been provided, the above description is illustrative and not restrictive. Many variations of the invention will become apparent to those of skill in the art upon review of this specification. The scope of the invention should, therefore, be determined not with reference to the above description, but instead should be determined with reference to the appended claims along with their full scope of equivalents.

All publications and patent documents cited in this application are incorporated by reference in their entirety for all purposes to the same extent as if each individual publication or patent document were so individually denoted.

We claim:

1. A composition comprising (1) detectably-labeled chromosome-specific paints prepared from *Hylobates concolor* chromosomes or chromosome fragments and (2) detectably-labeled chromosome-specific paints prepared from *Hylobates syndactylus* chromosomes or chromosome fragments.

2. The composition of claim 1, wherein the paints are labeled with from 1 to 3 labels selected from Cyanine-3, Cyanine-5, and fluorescein-isothiocyanate.

3. The composition of claim 1, further containing formamide.

4. A kit comprising (1) detectably labeled chromosome-specific paints prepared from *Hylobates concolor* chromosomes or chromosome fragments and (2) detectably labeled chromosome-specific paints prepared from *Hylobates syndactylus* chromosomes or chromosome fragments.

5. The kit of claim 4, further comprising at least one of: formamide, 4,6-diaminido-2-phenylindole (DAPI), anti-FITC antibody, fluorochrome-conjugated avidin, printed instructions for detecting a chromosomal aberration in a human chromosome by cross-species color banding photograph or drawing of a normal human karyotype stained with the detectably labeled chromosome paints.

6. The kit of claim 4, further comprising a photograph or drawing of a normal human karyotype stained with the detectably labeled chromosome paints.

7. The composition of claim 1 wherein the paints are labeled with at least one hapten species selected from the group consisting of biotin, digoxigenin, and fluorescein-isothiocyanate.

* * * * *